(12) United States Patent
Lee et al.

(10) Patent No.: US 11,266,983 B2
(45) Date of Patent: Mar. 8, 2022

(54) PILLAR STRUCTURE FOR BIOCHIP

(71) Applicants: MBD CO., LTD., Suwon-si (KR); SAMSUNG LIFE PUBLIC WELFARE FOUNDATION, Seoul (KR)

(72) Inventors: Don Jung Lee, Yongin-si (KR); Ho Jeong Song, Suwon-si (KR); Dong Woo Lee, Suwon-si (KR); Do Hyun Nam, Seoul (KR)

(73) Assignees: MBD Co., Ltd., Suwon-Si (KR); Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 16/061,277

(22) PCT Filed: Dec. 12, 2016

(86) PCT No.: PCT/KR2016/014500
§ 371 (c)(1),
(2) Date: Jun. 11, 2018

(87) PCT Pub. No.: WO2017/099544
PCT Pub. Date: Jun. 15, 2017

(65) Prior Publication Data
US 2018/0361373 A1    Dec. 20, 2018

(30) Foreign Application Priority Data
Dec. 11, 2015    (KR) .................. 10-2015-0177119

(51) Int. Cl.
*B01L 3/00*    (2006.01)
*B01J 19/00*    (2006.01)
(Continued)

(52) U.S. Cl.
CPC ............. *B01L 3/50* (2013.01); *B01J 19/0046* (2013.01); *B01L 3/5085* (2013.01);
(Continued)

(58) Field of Classification Search
CPC ........ B01L 3/50; B01L 3/5085; B01L 3/5088; B01L 2300/0848; B01L 2200/025;
(Continued)

(56) References Cited

U.S. PATENT DOCUMENTS

| | | | |
|---|---|---|---|
| 2001/0036674 A1 | 11/2001 | Indermuhle et al. | |
| 2006/0057580 A1* | 3/2006 | Zou ................... | B01L 3/502707 435/6.11 |

(Continued)

FOREIGN PATENT DOCUMENTS

| | | |
|---|---|---|
| EP | 2314436 A1 | 4/2011 |
| JP | 2004-122751 A | 4/2004 |

(Continued)

OTHER PUBLICATIONS

"The function and design method of the rib" by CROP (www.cropp.kr) on Jan. 30, 2015, and retrieved online from <<https://blog.naver.com/hopis/220257300135>> on Mar. 23, 2020.

*Primary Examiner* — Gautam Prakash
(74) *Attorney, Agent, or Firm* — Dentons US LLP (57) ABSTRACT

Technology for a pillar structure for a biochip is disclosed. The pillar structure for a biochip includes: a substrate portion having a plate structure; an insertion pillar portion formed in one piece with the substrate portion and protruding downward from a lower surface of the substrate portion so as to be inserted into a well; and a compensation pillar portion formed in one piece with the substrate portion, the compensation pillar portion corresponding to the insertion pillar portion and protruding upward from an upper surface of the substrate portion. Therefore, when the pillar structure (Continued)

is cooled during an injection molding process, the substrate portion is prevented from being partially recessed, and when samples are analyzed using microscopic images, accuracy and reliability may be improved.

2 Claims, 8 Drawing Sheets

(51) Int. Cl.
 *G01N 33/50* (2006.01)
 *C40B 60/12* (2006.01)
(52) U.S. Cl.
 CPC ............ *B01L 3/5088* (2013.01); *G01N 33/50* (2013.01); *B01J 2219/0047* (2013.01); *B01J 2219/00387* (2013.01); *B01J 2219/00509* (2013.01); *B01L 2200/025* (2013.01); *B01L 2200/0684* (2013.01); *B01L 2300/0819* (2013.01); *B01L 2300/0848* (2013.01); *B01L 2300/0893* (2013.01); *C40B 60/12* (2013.01)
(58) Field of Classification Search
 CPC ..... B01L 2200/0684; B01L 2300/0819; B01L 2300/0893; B01J 19/0046; B01J 2219/00387; B01J 2219/00509; B01J 2219/0047; C40B 60/12; G01N 33/50
 See application file for complete search history.

(56) References Cited

U.S. PATENT DOCUMENTS

| | | |
|---|---|---|
| 2013/0184182 A1 | 7/2013 | Lee et al. |
| 2014/0134652 A1 | 5/2014 | Honkanen et al. |

FOREIGN PATENT DOCUMENTS

| | | |
|---|---|---|
| KR | 10-2012-0026999 A | 3/2012 |
| KR | 10-2012-0044650 A | 5/2012 |
| KR | 10-2012-0132999 A | 12/2012 |
| KR | 10-1218986 B1 | 1/2013 |
| KR | 10-2013-0084394 A | 7/2013 |
| WO | 2005/042165 A1 | 5/2005 |
| WO | 2010/021306 A1 | 2/2010 |

* cited by examiner

PILLAR STRUCTURE FOR BIOCHIP

TECHNICAL FIELD

The present disclosure relates to a pillar structure for a biochip, and more particularly, to a pillar structure for a biochip which is configured to prevent a substrate portion from being partially recessed when the pillar structure is cooled during an injection molding process and to improve accuracy and reliability when samples are analyzed using microscopic images.

BACKGROUND ART

In general, biochips refer to microchips used to analyze genetic defects, protein distribution, reaction behaviors, or the like by placing biological micro-object samples such as DNA, proteins, or cells on small substrates.

Such a biochip includes: a pillar structure having a plurality of pillars formed on a substrate; and a well structure having a plurality of wells formed in a substrate. In general, the pillar structure and the well structure are formed by an injection molding method using a resin composition material.

However, according to techniques of the related art, as disclosed in Korean Patent Application Publication No. 10-2013-0084394, a pillar structure in which a plurality of pillars simply protrude from a surface of a substrate is used, and thus when the pillar structure is cooled after an injection molding process, the substrate undergoes non-uniform contraction, thereby having recessed portions.

In addition, as disclosed in Korean Patent Publication No. 10-1218986, according to techniques of the related art, a sample is directly placed on a substrate or pillars having a simple pillar structure and is then inserted into wells, and thus when external force or vibration is applied to a biochip, the sample is separated or damaged as the sample or the pillars collide with sidewalls of the wells.

In addition, if the diameter of the pillars is increased to reduce collision between the sidewalls of the wells and the pillars, when the pillars are inserted into the wells, air contained in the wells may not escape because of narrow gaps between the sidewalls of the wells and the pillars, and thus bubbles are formed in a culture solution filled in the wells. Such bubbles formed in the culture solution may wither or damage the sample.

DESCRIPTION OF EMBODIMENTS

Technical Problem

Provided is a pillar structure for a biochip which is configured to prevent a substrate portion from being partially recessed when the pillar structure is cooled during an injection molding process, improve accuracy and reliability when samples are analyzed using microscopic images, and reduce collision between a sidewall of a well and a pillar while suppressing the formation of bubbles in the well when the pillar is inserted into the well.

Solution to Problem

According to an aspect of the present disclosure, a pillar structure for a biochip includes: a substrate portion having a plate structure; an insertion pillar portion formed in one piece with the substrate portion and protruding downward from a lower surface of the substrate portion so as to be inserted into a well; and a compensation pillar portion formed in one piece with the substrate portion, the compensation pillar portion corresponding to the insertion pillar portion and protruding upward from an upper surface of the substrate portion.

In an embodiment, the compensation pillar portion may have a diameter having a ratio to a diameter of the insertion pillar portion within a range of 1 to 1.3.

In an embodiment, the insertion pillar portion may include: a first pillar portion protruding downward from the lower surface of the substrate portion; and a second pillar portion protruding downward from a lower surface of the first pillar portion and configured to receive a sample, wherein the first pillar portion may have a diameter less than a diameter of the well but greater than a diameter of the second pillar portion.

In this case, the compensation pillar portion may have a diameter having a ratio to a diameter of the second pillar portion within a range of 1 to 1.3.

In an embodiment, the pillar structure may include a plurality of insertion pillar portions and a plurality of compensation pillar portions respectively corresponding to the plurality of insertion pillar portions, wherein each of at least some of the plurality of insertion pillar portions includes the first pillar portion and the second pillar portion.

Advantageous Effects of Disclosure

According to the present disclosure, an insertion pillar portion is formed on a surface of a substrate portion of a pillar structure for a biochip, and a compensation pillar is formed on the other surface of the substrate portion. Therefore, when the substrate portion is cooled during an injection molding process, the substrate portion may be prevented from being partially recessed, and when samples are analyzed using microscopic images, accuracy and reliability may be improved.

In addition, the diameter of an upper end portion of the insertion pillar portion to be inserted into a well is greater than the diameter of a lower end portion of the insertion pillar portion on which a sample is to be placed, thereby preventing the formation of bubbles in the well when the insertion pillar portion is inserted into the well, and reducing collision between a sidewall of the well and the insertion pillar portion and preventing separation of the sample from the insertion pillar portion when external force or vibration is applied to the biochip.

In addition, those of ordinary skill in the art will clearly understand from the following description that various embodiments of the present disclosure may also be useful to solve various technical problems not mentioned above.

BEST MODE

Hereinafter, embodiments of the present disclosure will be described in detail with reference to the accompanying drawings so that methods for solving technical problems of the present disclosure may be clearly understood. However, detailed descriptions relating to well-known techniques may be omitted in order not to unnecessarily obscure subject matters of the present disclosure. In addition, terms used herein are defined in consideration of functions of the present disclosure, but the terms may vary according to the intention of designer or manufactures, precedents, or the like. Therefore, these terms should be construed based on the entirety of the present disclosure.

Figure 1:
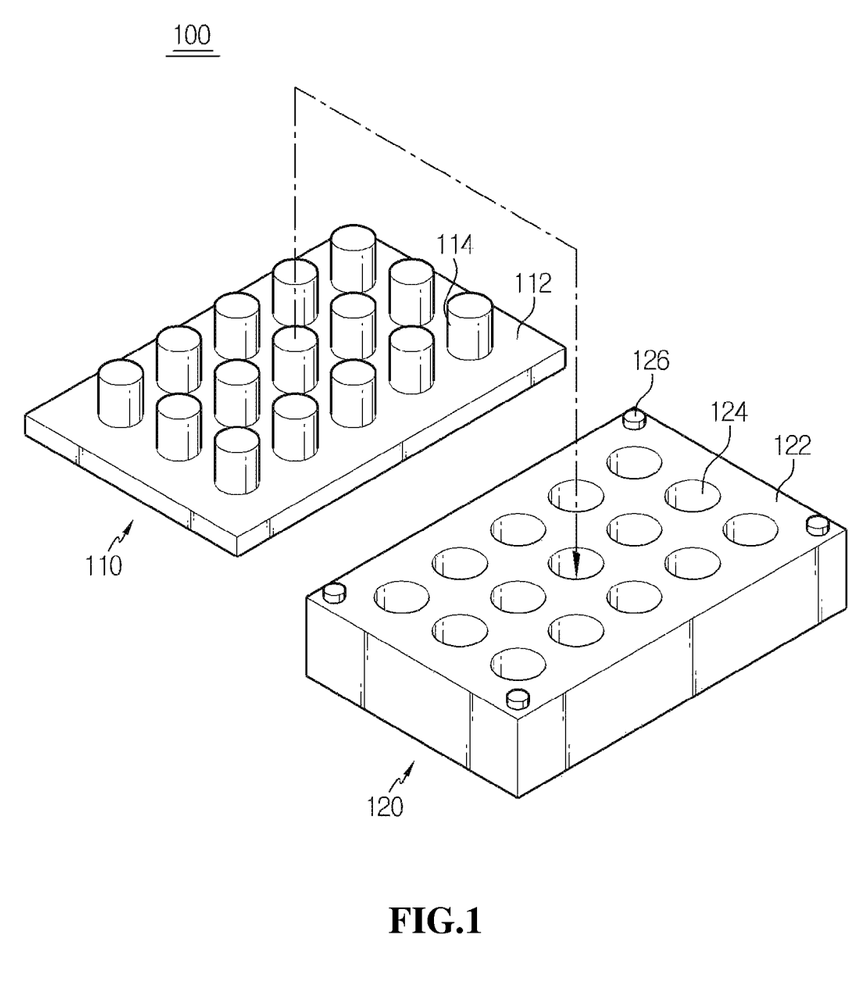
FIG. 1 is a view illustrating an example of a biochip to which the present disclosure is applicable.

FIG. 1 is a view illustrating an example of a biochip 100 to which the present disclosure is applicable.

As illustrated in FIG. 1, the biochip 100 includes a pillar structure 110 and a well structure 120. In general, the pillar structure 110 has a structure in which a plurality of pillars 114 are formed on a surface of a plate-shaped substrate 112. A sample including biological micro-objects such as DNA, proteins, or cells is placed on each of distal end portions of the pillars 114. The well structure 120 has a structure in which a plurality of wells 124 configured to receive the pillars 114 of the pillar structure 110 are formed in a surface of a plate-shaped substrate 122. A certain amount of a culture solution, a reagent, or the like is filled in each of the wells 124. The pillar structure 110 is coupled to the well structure 120, and then the sample placed on the pillars 114 is placed in the wells 124. In addition, the well structure 120 may include spacer members 126. The spacer members 126 are placed between coupling surfaces of the pillar structure 110 and the well structure 120 such that the wells 124 may be prevented from being sealed airtight when the pillar structure 110 and the well structure 120 are coupled to each other.

Figure 2:
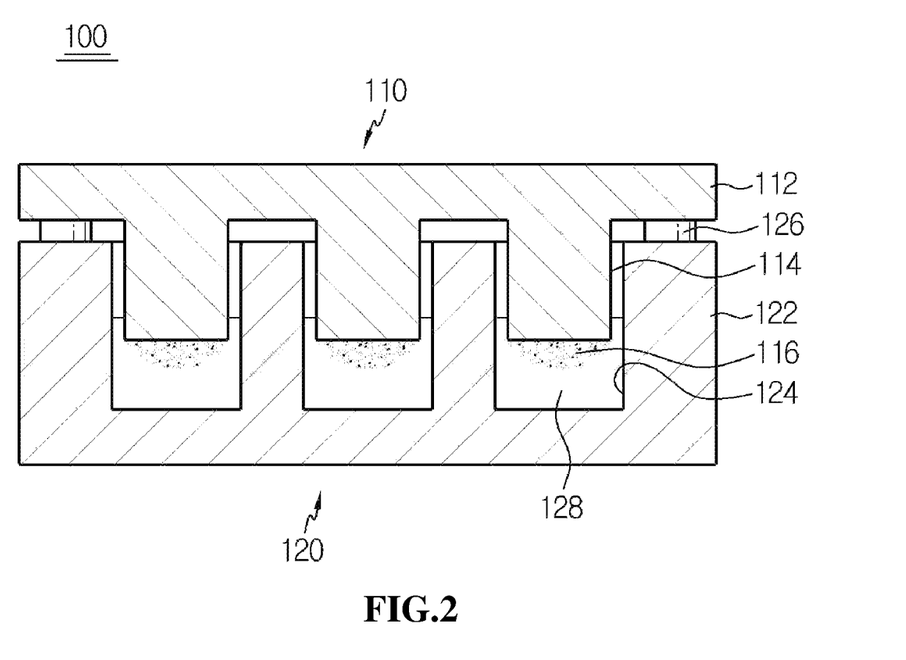
FIG. 2 is a cross-sectional view illustrating an example state in which a pillar structure and a well structure are coupled to each other.

FIG. 2 is a cross-sectional view illustrating an example state in which the pillar structure 110 and the well structure 120 are coupled to each other.

As illustrating in FIG. 2, when the pillar structure 110 and the well structure 120 are coupled to each other, each of the pillars 114 is inserted into a corresponding one of the wells 124, and a sample 116 placed on the pillars 114 is immersed in a culture solution 128 contained in the wells 124. After a certain period of time, an experimenter analyzes the sample 116 placed on the pillars 114 of the pillar structure 110 using a device such as a fluorescence microscope. Therefore, the pillar structure 110 is formed of a resin composition material having high light transmittance. For example, the pillar structure 110 may be formed of a resin composition material including polystyrene, maleic anhydride, or the like. In addition, when the pillar structure 110 is actually manufactured, the resin composition material is melted, injection-molded, and cooled according to an injection molding method.

Figure 3:
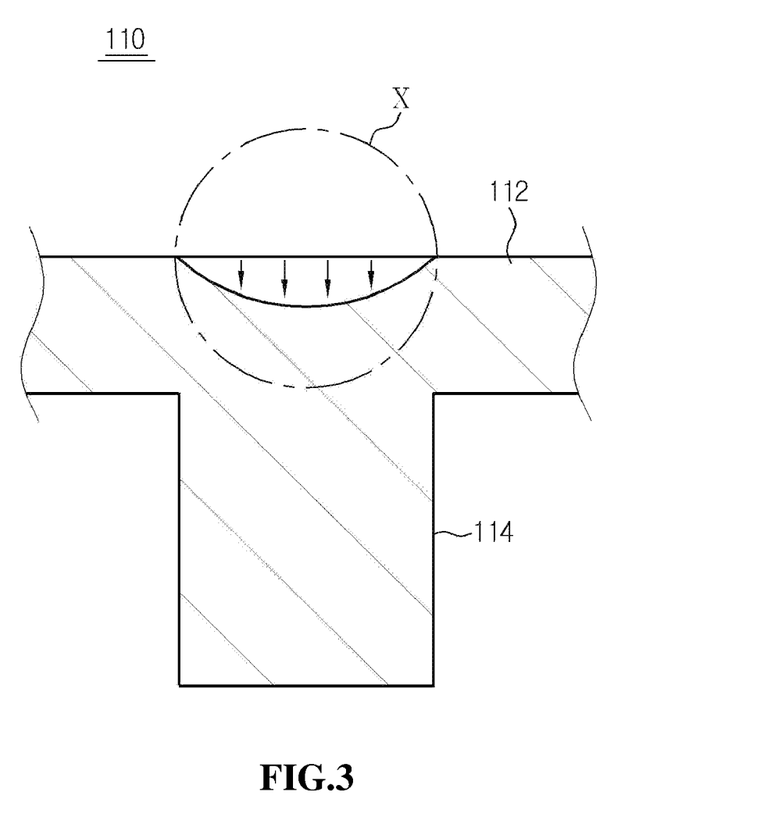
FIG. 3 is a cross-sectional view illustrating an example of the pillar structure formed by an injection molding method.

FIG. 3 is a cross-sectional view illustrating an example of the pillar structure 110 formed by an injection molding method.

As illustrated in FIG. 3, when the pillar structure 110 is manufactured by an injection molding method, the pillar structure 110 contracts in the entire region thereof during cooling after injection molding. At this time, the amount of contraction of the pillars 114 provided on a lower surface of the substrate portion 112 of the pillar structure 110 has an effect on the substrate portion 210, and thus portions X of an upper surface of the substrate portion 112 located above the pillars 114 are recessed. The recessed portions X of the substrate portion 112 cause scattering of light or scattered reflection of light and thus distort microscopic images, thereby making it difficult to analyze samples.

Figure 4:
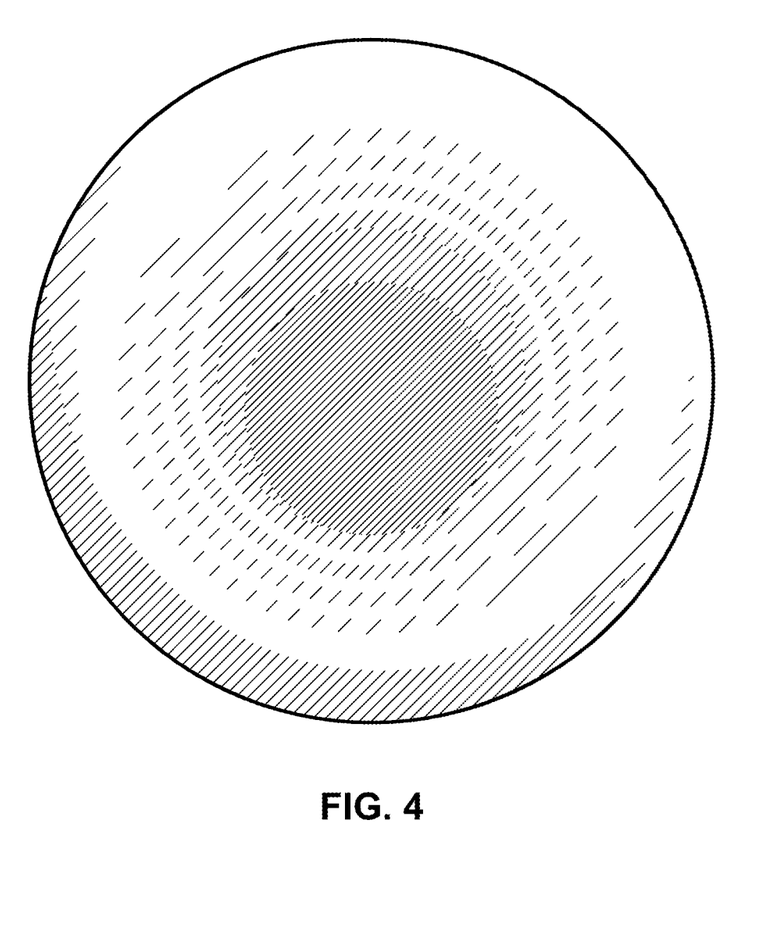
FIG. 4 is a fluorescence microscopic image of the pillar structure shown in FIG. 3.

FIG. 4 is a fluorescence microscopic image of the pillar structure 110 shown in FIG. 3.

As illustrated in FIG. 4, if a distal end portion of a pillar 114 of the pillar structure 110 is observed with a fluorescence microscope when the substrate portion 112 is recessed, a fluorescence microscopic image has a distortion such as a shadow because of scattering or scattered reflection of light at a recessed portion X of the substrate portion 112.

Therefore, according to the present disclosure, a pillar structure having a new configuration is applied to a biochip to prevent a substrate portion from being recessed during an injection molding process of the pillar structure and to improve accuracy and reliability when samples are analyzed using the biochip.

Figure 5:
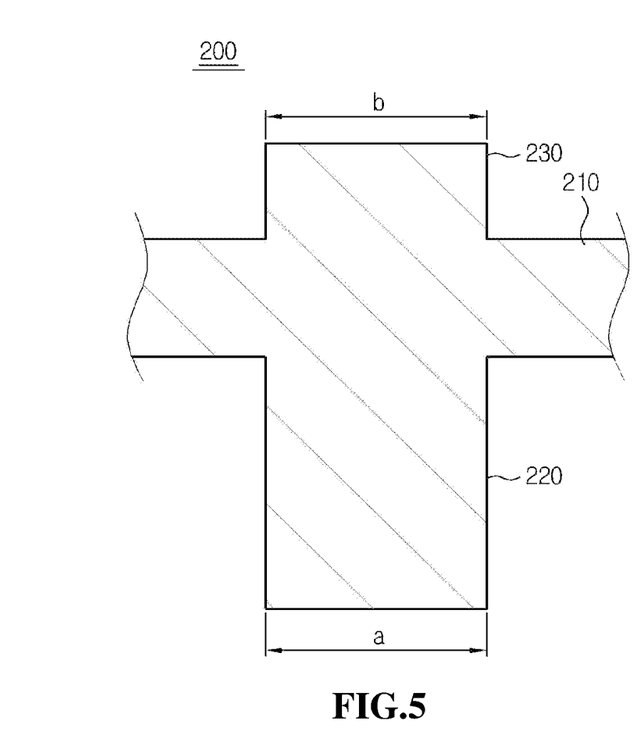
FIG. 5 is a cross-sectional view illustrating a pillar structure according to an embodiment of the present disclosure.

FIG. 5 is a cross-sectional view illustrating a pillar structure 200 according to an embodiment of the present disclosure.

As illustrated in FIG. 5, the pillar structure 200 of the embodiment of the present disclosure may include a substrate portion 210, an insertion pillar portion 220, and a compensation pillar portion 230. The substrate portion 210 has a plate structure and forms a base of the pillar structure 200.

The insertion pillar portion 220 is formed in one piece with the substrate portion 210 and protrudes downward from a lower surface of the substrate portion 210, and when the pillar structure 200 is coupled to a well structure (for example, refer to reference numeral 120 in FIG. 1), the insertion pillar portion 220 is inserted into a well (for example, refer to reference numeral 124 in FIG. 1) of the well structure. A sample is placed on a distal end portion of the insertion pillar portion 320. A dispersion material layer (not shown) may be applied to the distal end portion of the pillar portion 320 for easy placement of the sample. The dispersion material layer is formed of a porous material permeable to a culture solution or a reagent. For example, the dispersion material layer may include a material such as sol-gel, hydrogel, alginate gel, organogel, xerogel, or collagen. In this case, the sample is placed by dispersing the sample in the dispersion material layer.

The compensation pillar portion 230 is formed in one piece with the substrate portion 210. The compensation pillar portion 230 protrudes upward from an upper surface of the substrate portion 210 and corresponds to the insertion pillar portion 220. In this manner, the compensation pillar portion 230 is provided on a portion of the substrate portion 210 expected to be recessed, and thus during cooling after injection molding, the compensation pillar portion 230 compensates for the amount of contraction of the insertion pillar portion 220, thereby preventing the substrate portion 210 from being recessed.

In this case, the compensation pillar portion 230 is required to have a diameter having a ratio to the diameter of the insertion pillar portion 220 within the range of 1 to 1.3.

For example, if the diameter (b) of the compensation pillar portion 230 is less than the diameter (a) of the insertion pillar portion 220, that is, the diameter ratio b/a of the compensation pillar portion 230 to the insertion pillar portion 220 is less than 1, light rays incident on a microscope lens from a side of the compensation pillar portion 230 and the substrate portion 210 through a distal end portion of the insertion pillar portion 220 may have different optical paths, and thus microscopic images may be distorted. Conversely, if the diameter (b) of the compensation pillar portion 230 is greater than 1.3 times the diameter (a) of the insertion pillar portion 220, that is, the diameter ratio b/a of the compensation pillar portion 230 to the insertion pillar portion 220 is greater than 1.3, it is difficult to highly integrate a biochip, and an unnecessary material loss may occur. In addition, an upper surface of the compensation pillar portion 230 may be recessed.

Figure 6:
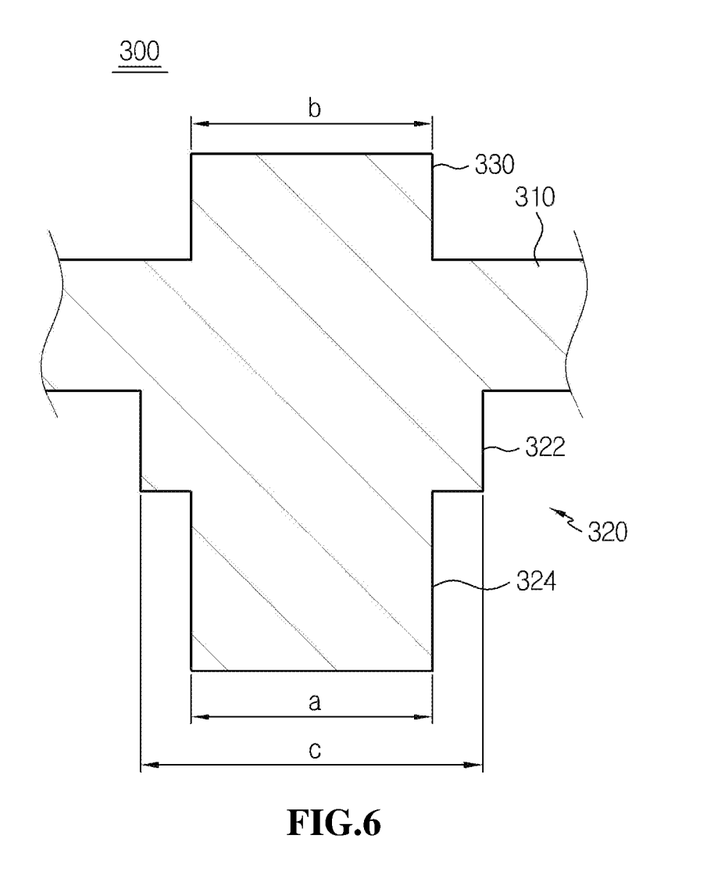
FIG. 6 is a cross-sectional view illustrating a pillar structure according to another embodiment of the present disclosure.
Figure 7:
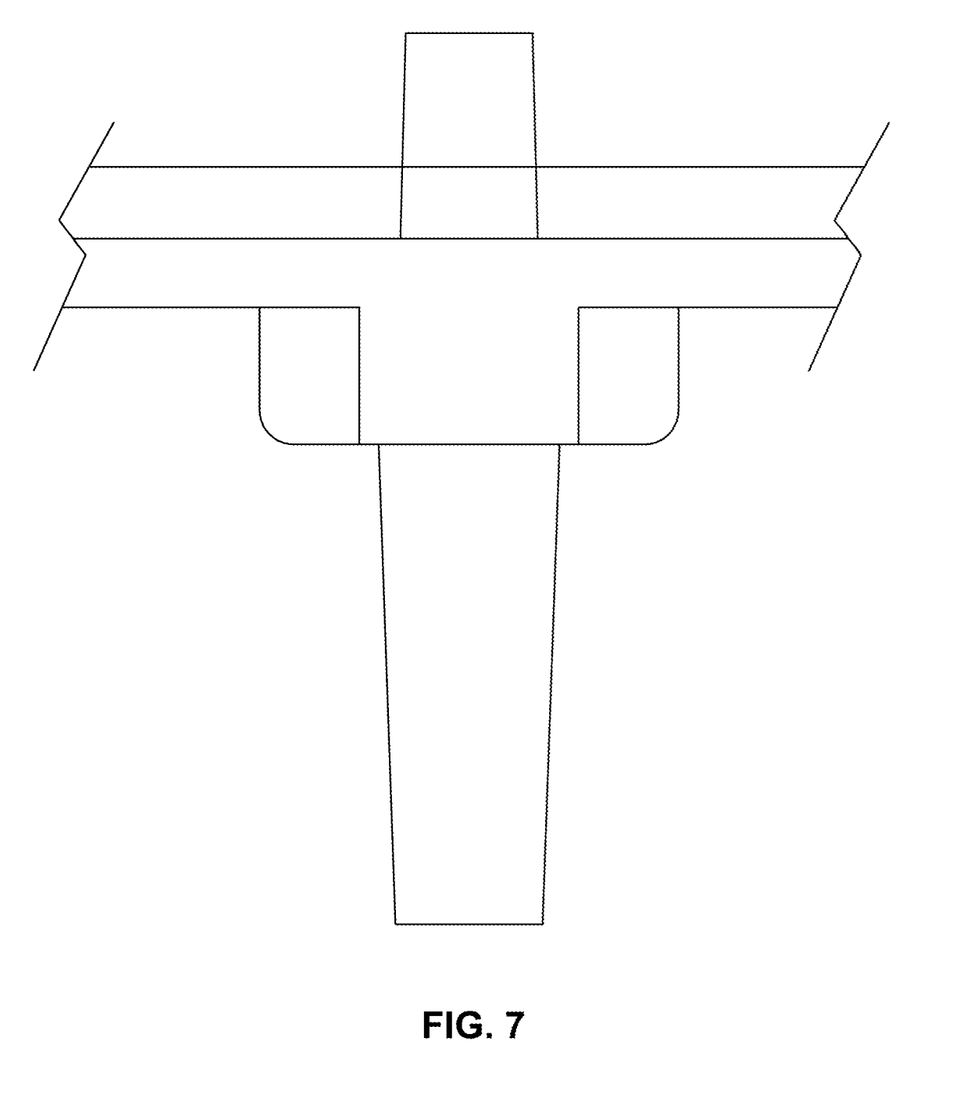
FIG. 7 is an image of an actually implemented pillar structure.

FIG. 6 is a cross-sectional view illustrating a pillar structure 300 according to another embodiment of the present disclosure. FIG. 7 is an image of an actually implemented pillar structure.

As illustrated in FIGS. 6 and 7, the pillar structure 300 of an embodiment of the present disclosure includes a substrate portion 310, an insertion pillar portion 320, and a compensation pillar portion 330. The substrate portion 310, the insertion pillar portion 320, and the compensation pillar portion 330 respectively correspond to the substrate portion 210, the insertion pillar portion 220, and the compensation pillar portion 230 illustrated in FIG. 5.

Particularly, the insertion pillar portion 320 includes a first pillar portion 322 and a second pillar portion 324. The first pillar portion 322 protrudes downward from a lower surface of the substrate portion 310. The second pillar portion 324 protrudes downward from a lower surface of the first pillar portion 322, and a sample is placed on a distal end portion of the second pillar portion 324. The first pillar portion 322 and the second pillar portion 324 form a step on the insertion pillar portion 320. That is, the first pillar portion 322 has a diameter (c) less than the diameter of a well into which the first pillar portion 322 will be inserted, but the diameter (c) of the first pillar portion 322 is greater than the diameter (a) of the second pillar portion 324.

If the insertion pillar portion 320 has a simple pillar shape as described above, the insertion pillar portion 320 may collide with a sidewall of the well due to external force or vibration applied to a biochip, and thus the sample may be separated or damaged. Conversely, if the diameter of the insertion pillar portion 320 is increased to reduce collision between the sidewall of the well and the insertion pillar portion 320, when the insertion pillar portion 320 is inserted into the well, air contained in the well may not escape because of a narrow gap between the sidewall of the well and the insertion pillar portion 320, and thus bubbles may be formed in a culture solution filled in the well. Bubbles formed in the culture solution may wither or damage the sample.

Therefore, the formation of bubbles may be prevented while reducing collision between the sidewall of the well and the insertion pillar portion 320 by adjusting the diameter (c) of an upper end portion of the insertion pillar portion 320 to be greater than the diameter (a) of a lower end portion of the insertion pillar portion 320.

In this case, the compensation pillar portion 330 may have a diameter having a ratio to the diameter of the second pillar portion 324 within the range of 1 to 1.3.

The pillar structure 300 may include a plurality of insertion pillar portions on the substrate portion 310, and a plurality of compensation pillar portions respectively corresponding to the plurality of insertion pillar portions. In this case, it may not be necessary that all the plurality of insertion pillar portions have stepped portions. That is, only some of the plurality of insertion pillar portions may have first pillar portions 322 and second pillar portions 324 that form stepped portions. For example, only outermost insertion pillar portions or corner pillar insertion portions of m×n insertion pillar portions 320 formed on the substrate portion 310 of the pillar structure 300 may include first pillar portions 322 and second pillar portions 324, and the other insertion pillar portions 320 may have a general pillar shape.

In the embodiments of the present disclosure, the terms "upper surface" and "lower surface" or "upward" and "downward" are relative terms used to describe relative positions and structures of the insertion pillar portions and the compensation pillar portions.

Figure 8:
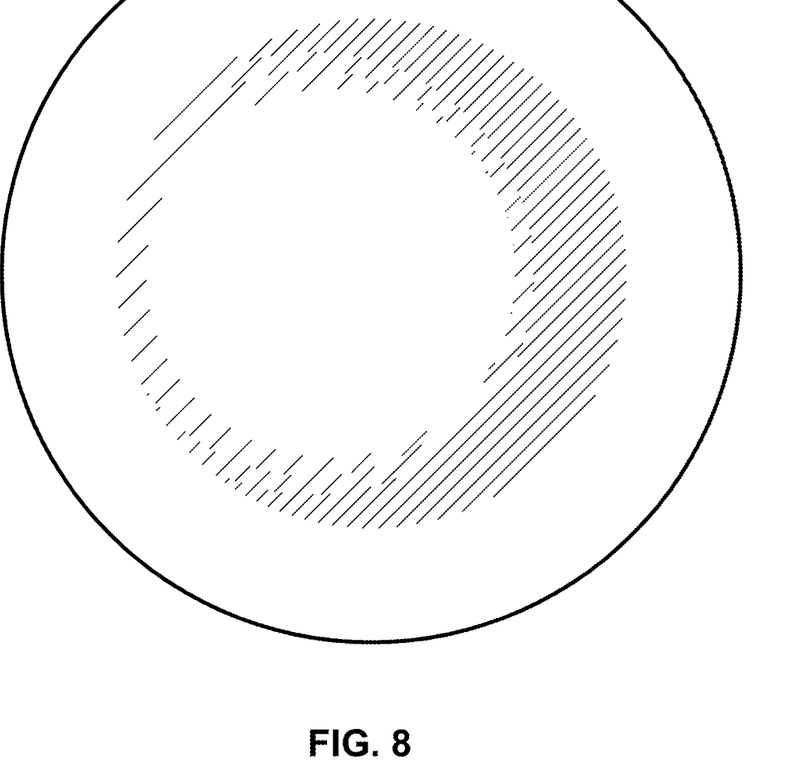
FIG. 8 is a fluorescence microscopic image of a pillar structure of the present disclosure.

FIG. 8 is a fluorescence microscopic image of a pillar structure of the present disclosure.

As illustrated in FIG. 8, the fluorescence microscopic image of the pillar structure of the present disclosure does not have a distortion such as a shadow unlike that shown in FIG. 4. That is, in the pillar structure of the present disclosure, a compensation pillar portion is provided on a portion of a substrate portion expected to be recessed, in order to compensate for contraction of an insertion pillar portion when the pillar structure is cooled after an injection molding process, thereby preventing the substrate portion from being recessed and microscopic images from being distorted, and improving accuracy and reliability when samples are analyzed using microscopic images.

In addition, according to the present disclosure, the diameter of an upper end portion of the insertion pillar portion to be inserted into a well is greater than the diameter of a lower end portion of the insertion pillar portion on which a sample is to be placed, thereby preventing the formation of bubbles in the well when the insertion pillar portion is inserted into the well, and reducing collision between a sidewall of the well and the insertion pillar portion and preventing separation of the sample from the insertion pillar portion even when external force or vibration is applied to a biochip. Furthermore, in relevant technical fields as well as in the technical field to which the present disclosure pertains, various embodiments of the present disclosure may be useful to solve various technical problems in addition to those problems mentioned in the present disclosure.

Specific embodiments of the present disclosure have been described. However, those of ordinary skill in the art will clearly understand that various modifications could be made within the scope of the present disclosure. Therefore, the embodiments described herein should be considered in a descriptive sense only and not for purposes of limitation. That is, the scope of the present disclosure should be defined by the following claims, and all differences within equivalents ranges of the scope of the present disclosure should be considered as being included in the scope of the present disclosure.

The invention claimed is:

1. A pillar structure for a biochip, comprising:
a substrate portion having a plate structure;
an insertion pillar formed downward on a lower surface of the substrate portion about a vertical axis, the insertion pillar being shaped so as to be inserted into a well; and
a compensation pillar formed upward on an upper surface of the substrate portion about the vertical axis and opposite to the insertion pillar, wherein the substrate portion, the insertion pillar, and the compensation pillar comprise a light transmitting melted resin composition material, wherein a diameter of the compensation pillar is greater than a diameter of the insertion pillar, and wherein the compensation pillar is configured to prevent the upper surface of the substrate from being recessed.

2. The pillar structure of claim 1, wherein a ratio of the diameter of the compensation pillar to the diameter of the insertion pillar is greater than 1 but less than 1.3.

* * * * *